United States Patent [19]

Rebsdat et al.

[11] Patent Number: 4,458,032

[45] Date of Patent: Jul. 3, 1984

[54] SILVER CATALYSTS, A PROCESS FOR THEIR PREPARATION, AND THEIR USE IN PREPARING ETHYLENE OXIDE

[75] Inventors: Siegfried Rebsdat, Burg; Sigmund Mayer, Burgkirchen/Alz; Josef Alfranseder, Hofschallern, all of Fed. Rep. of Germany

[73] Assignee: Hoechst Aktiengesellschaft, Frankfurt am Main, Fed. Rep. of Germany

[21] Appl. No.: 508,475

[22] Filed: Jun. 27, 1983

[30] Foreign Application Priority Data

Jun. 30, 1982 [DE] Fed. Rep. of Germany ....... 3224322
Jun. 30, 1982 [DE] Fed. Rep. of Germany ....... 3224323

[51] Int. Cl.$^3$ ............................................. B01J 23/50
[52] U.S. Cl. .................................... 502/348; 502/344; 502/347
[58] Field of Search ....................... 252/476, 463, 461; 502/344, 347, 348

[56] References Cited

U.S. PATENT DOCUMENTS

| | | | |
|---|---|---|---|
| 4,010,115 | 3/1977 | Nielsen et al. | 252/476 |
| 4,226,782 | 10/1980 | Hayden et al. | 252/476 |
| 4,305,844 | 12/1981 | Vangermain et al. | 252/476 |
| 4,389,338 | 6/1983 | Mitsuhata et al. | 252/476 |

*Primary Examiner*—Delbert E. Gantz
*Assistant Examiner*—Anthony McFarlane
*Attorney, Agent, or Firm*—Curtis, Morris & Safford

[57] ABSTRACT

Silver catalysts, useful for the oxidation of ethylene to ethylene oxide, contain 3–20 percent by weight of silver and 0.003–0.05 percent by weight of potassium, rubidium, cesium, or a mixture thereof as a promoter present on a heat-resistant porous support to which they have been applied by several impregnating steps.

12 Claims, No Drawings

SILVER CATALYSTS, A PROCESS FOR THEIR PREPARATION, AND THEIR USE IN PREPARING ETHYLENE OXIDE

The invention relates to silver catalysts which consist of silver and promoter on a heat-resistant porous support material. The invention also relates to a process for preparing these catalysts and to their use in the preparation of ethylene oxide by oxidizing ethylene with oxygen.

The large-scale production of ethylene oxide involves the direct oxidation of ethylene with oxygen on a silver catalyst. The process is described in general in Kirk-Othmer, Encyclopedia of Chemical Technology, volume 9, pages 432 to 471, John Wiley, London/New York, 1980.

An ethylene- and oxygen-containing gas enters the reactor at the top. The reactor consists of a bundle of several thousand tubes which are 6 to more than 10 m long. The gas flows over the catalyst present in the tubes, preferably at a temperature of 200° to 300° C. under an overpressure of 1 to 2 mPa, and 5 to 20% of the starting ethylene reacts.

Not only is ethylene oxide formed, but a considerable proportion of the ethylene, namely about 25%, is oxidized to carbon dioxide and water (total oxidation), as the following equations are intended to show:

Ethylene oxide formation: $2C_2H_4 + O_2 \rightarrow 2C_2H_4O$
Total oxidation: $C_2H_4 + 3O_2 \rightarrow 2CO_2 + 2H_2O$ For temperature control and heat dissipation, the tubes are surrounded by a heat transfer medium which carries the evolved heat out of the reactor. On leaving the reactor, the reaction gas, which contains ethylene oxide and carbon dioxide, passes into the working-up zone where the ethylene oxide and carbon dioxide are separated off. The gas, now freed from ethylene oxide and carbon dioxide, is again enriched with ethylene and oxygen and returned to the reactor. It is a continuous cycle process involving heterogeneous catalysis.

The catalyst used is a supported silver catalyst. The quality of such a catalyst is essentially determined by its selectivity, its activity and its operating life.

The selectivity is the molar percentage of converted ethylene which reacts to give ethylene oxide.

The activity is characterized by the ethylene oxide concentration at the reactor outlet under otherwise constant conditions (for example temperature, pressure, gas flow rate, amount of catalyst). The higher the ethylene oxide concentration, the higher is the activity. In other words: the lower the temperature required for a certain ethylene oxide concentration, the higher is the activity.

The quality of a catalyst is not only determined by its activity and selectivity but also by its operating life. The effectiveness of catalysts in use decreases with time, i.e. activity and selectivity are constantly decreasing, so that a catalyst will have to be changed sooner or later, depending on its rate of aging. However, to change a catalyst is a complicated and expensive step which is associated with loss of material. The old catalyst has to be emptied out of several thousand reactor tubes tube by tube, and they then have to be recharged with the new catalyst. This procedure can take several weeks, and involves a corresponding loss of production. The old catalyst also needs to be reworked to recover the silver. In such a recovery process, some loss of silver is unavoidable. The support material cannot be reused.

The preparation of a new silver catalyst also involves losses of silver. Large amounts of silver have to be transported, insured and financed and may attract duty. A good silver catalyst for the preparation of ethylene oxide by direct oxidation of ethylene thus should have a very high activity and selectivity and also a long operating life.

The preparation of supported silver catalysts per se has been known for a long time. They are preferably prepared by the following method:

The support material is soaked with a solution of a silver salt. The soaked support material is dried, the silver salt settling out on the support material. The support material thus impregnated with silver salt is subjected to conditions under which the silver salt decomposes to form elemental silver which is present on the support in finely divided form. This step may be carried out purely thermally by heating to about 170° to 400° C. or by means of reducing agents such as formaldehyde.

It has been known for a long time that the effectiveness of silver catalysts can be improved by means of so-called promoters, which is the name given to chemical elements which, when used in an amount as low as 10 to 1000 mg/kg, relative to the amount of silver, increase the effectiveness. The elements potassium, rubidium and cesium have been found to be particularly effective promoters. Selectivities of about 80%, combined with good activity, can be obtained with these promoters.

In recent years it has been found that, in preparing new supported silver catalysts of high effectiveness, not only the promoter itself is important, but also the manner in which it is applied to the support material, specifically the time it is applied in respect of when the silver is applied, and it also appears to be of some importance when the applied silver compound is reduced to metallic silver.

German Offenlegungsschrift No. 2,448,449 says that it is advantageous to deposit onto the support the entire amount of promoter first and only then the entire amount of silver, and then to reduce the deposited silver compound to metallic silver. In contrast, German Offenlegungsschriften Nos. 2,733,688 and 3,011,717 and British Pat. No. 2,002,252 recommend that new supported silver catalysts having improved effectiveness should be prepared by applying the total amount of silver in a first impregnating step and the total amount of promoter in a subsequent, second impregnating step, the silver compound applied being reduced after the first impregnating step under partly special conditions. In addition to these two methods, it is also known to apply the silver and promoter to the support material simultaneously. This way of preparing new silver catalysts of improved effectiveness is described in German Offenlegungsschriften Nos. 2,300,512, 2,734,912, 2,951,969 and 2,951,970.

The silver catalyst disclosed by German Offenlegungsschrift No. 2,300,512 consists of silver in an amount of 1.5 to 20% by weight and potassium, rubidium and/or cesium as promoter in an amount of 0.001 to 0.05% by weight on a heat-resistant porous support material, all weight percentages being relative to the weight of the catalyst (total weight of the catalyst), and is prepared by applying the silver and the promoter to the support simultaneously in the form of the respective impregnating solutions. The silver compound present on the support material is thermally converted (reduced) into metallic silver.

Owing to the promoters used, namely potassium, rubidium or cesium, this silver catalyst has a relatively good selectivity. Nevertheless, further attempts have been made to use the method of depositing onto the support material these promoters simultaneously with the silver to increase still further the selectivity and to improve the remaining important properties, such as, in particular, the activity and operating life. With this intention, said German Offenlegungsschriften Nos. 2,734,912 and 2,951,969 propose the use of a special impregnating solution, and said German Offenlegungsschrift No. 2,951,970 proposes treatment of the impregnated and activated catalyst in a mill to remove from its surface 1 to 10% by weight, which is said to lead to a long operating life.

A number of publications, for example German Offenlegungsschriften Nos. 2,454,972, 2,640,540, 2,723,918, 2,819,595 and 2,820,170, finally note that new supported silver catalysts having improved effectiveness are obtained when, in addition to the silver, several specific promoter metals are applied to the support material regardless of the order in which silver and promoter are deposited onto the support material.

The state of the art concerning the method of applying silver and promoter to the support material and the reduction of the applied silver compound to metallic silver shows that there already are several existing methods which are said to lead to effective supported silver catalysts. There is, nevertheless, a need for new silver catalysts having good properties, in particular for silver catalysts which have a high activity and selectivity and a long operating life, in particular since, in part, the known methods of preparation require special impregnating steps, special reductions and/or subsequent special treatments of the finished catalyst.

It was then found, surprisingly, that supported silver catalysts having a high activity and selectivity and a long operating life are obtained by performing the simultaneous application of silver and promoter in the required amounts to the support material not in one stage, but in two stages, and applying in each stage a well-defined proportion of the total amount of silver and promoter. It could not have been foreseen that specifically this variant of the simultaneous application of silver and promoter would have such a great effect, in particular since German Offenlegungsschrift No. 2,951,970 pays no attention to any repeated impregnating of the support with suitable impregnating solutions for the simultaneous application of the required amount of silver and promoter and the effectiveness of the catalyst can allegedly only be increased by means of the process described there of after-treating the catalyst to remove its surface skin.

It was also found that silver catalysts having a high activity and selectivity and a long operating life are surprisingly also obtained by applying silver and potassium, rubidium and/or cesium as promoter to the support material by first applying the total amount of silver and only a fraction of the total amount of promoter and then the remainder (of the total amount) of promoter.

In the silver catalyst of the invention, which consists of silver in an amount of 3 to 20% by weight and potassium, rubidium and/or cesium as a promoter in an amount of 0.003 to 0.05% by weight on a heat-resistant porous support material, all the weight percentages being relative to the weight of the catalyst (weight of the finished catalyst or total weight of the catalyst), the silver and promoter having been applied to the support material in the form of impregnating solutions and the applied silver compound having been reduced to metallic silver, the application of silver and promoter and the reduction have been carried out by one of the two following methods:

(a) simultaneous application of 55 to 85% by weight of the total amount of silver and 15 to 45% by weight of the total amount of promoter in a first impregnating step, (b) drying of the product obtained in step (a), (c) simultaneous application of the rest of the total amount of silver and promoter in a second impregnating step to the product obtained in step (b), and (d) heating of the product obtained in step (c) to reduce the applied silver compound to metallic silver, or (a') simultaneous or successive application of the total amount of silver and 15 to 45% by weight of the total amount of promoter in, respectively, one or two impregnating steps, (b') heating of the product obtained in step (a') to reduce the applied silver compound to metallic silver, (c') application of the rest of the total amount of promoter in a further impregnating step to the product obtained in step (b'), and (d') drying of the product obtained in step (c').

The novel process for preparing a silver catalyst by applying the silver and the promoter to the support material in the form of impregnating solutions and reducing the applied silver compound to metallic silver comprises being carried out by one of the two following methods:

(a) simultaneous application of 55 to 85% by weight of the total amount of silver and 15 to 45% by weight of the total amount of promoter in a first impregnating step, (b) drying of the product obtained in step (a), (c) simultaneous application of the rest of the total amount of silver and promoter in a second impregnating step to the product obtained in step (b), and (d) heating of the product obtained in step (c) to reduce the applied silver compound to metallic silver, or (a') simultaneous or successive application of the total amount of silver and 15 to 45% by weight of the total amount of promoter in, respectively, one or two impregnating steps, (b') heating of the product obtained in step (a') to reduce the applied silver compound to metallic silver, (c') application of the rest of the total amount of promoter in a further impregnating step to the product obtained in step (b'), and (d')drying of the product obtained in step (c').

The amount of silver is preferably 7 to 14% by weight and the amount of promoter 0.008 to 0.035% by weight, in each case relative to the weight of the catalyst.

The promoter is preferably cesium.

In the first method of the invention, preferably 60 to 75% by weight of the total amount of silver and 25 to 40% by weight of the total amount of promoter are applied in step (a) and the rest of the total amount of silver and promoter in step (c). In the second method of the invention, preferably 20 to 35% by weight of the total amount of promoter are applied in step (a').

The customary, commercially available heat-resistant and porous materials are possible for use as support material for the silver catalysts of the invention. These materials are inert even under the reaction conditions prevailing in the oxidation of ethylene, and in the presence of the chemical compounds used. The support material for preparing the silver catalysts of the invention is not critical, examples of suitable supports being carbon, corundum, silicon carbide, silicon dioxide, aluminum oxide and mixtures of aluminum oxide and silicon dioxide. $\alpha$-alumina is preferred, since it has a largely uniform pore diameter. It has a specific surface area of 0.1 to 1 $m^2/g$, preferably 0.2 to 0.6 $m^2/g$ (measured by the well-known B.E.T. method), a specific pore volume of 0.1 to 1 $cm^3/g$, preferably 0.2 to 0.6 $cm^3/g$ (measured by the well-known mercury or water adsorption method), an apparent porosity of 20 to 70% by volume, preferably 40 to 60% by volume (measured by the well-known mercury or water adsorption method), a mean pore diameter of 0.3 to 15 $\mu m$, preferably 1 to 10 $\mu m$, and a percentage of pores having a diameter of 0.03 to 10 $\mu m$ of at least 50% by weight (as is well-known, the pore diameter and pore diameter distribution are determined from the specific surface area and apparent porosity).

The support material is advantageously used in the form of granules, spheres, rings, pellets or the like. Examples of preferred support materials made of, or containing, $\alpha$-alumina are the types sold by Norton Company, U.S.A., under the labels SA 5551 and SA 5552 and the SAHM types sold by United Catalyst, U.S.A.

In the invention silver and promoter are applied to the support material by means of the known impregnating process, in which the support material is brought into contact with, preferably soaked by dipping in, solutions which consist of a solvent and an amount of silver compound and/or promoter compound sufficient for the silver deposition and for the promoter deposition on the support material, and the support material is then separated from excess solution and dried.

In the first method of the invention, the support material is first impregnated in such a way that 55 to 85% by weight, preferably 60 to 75% by weight, of the total amount of silver and 15 to 45% by weight, preferably 25 to 40% by weight, of the total amount of promoter are applied. After this first impregnating step the remainder (to the respective total amount) of silver and promoter is applied to the dried support material in a second impregnating step. The solutions for the two impregnating steps of the invention accordingly essentially consist of a solvent and an adequate amount of silver compound and promoter compound.

In the second method of the invention, the support material is impregnated in step (a') in such a way that the total amount of silver but only 15 to 45% by weight, preferably 20 to 35% by weight, of the total amount of promoter are applied. This can be achieved by impregnating the support material first with a solution containing at least one silver compound and then with a solution containing at least one promoter compound (variant 1), or with a solution which contains at the same time at least one silver compound and at least one promoter compound (simultaneous deposition of silver and promoter compound, which is variant 2). The solutions for the impregnating step (a') accordingly essentially consist of a solvent and an adequate amount of silver compound or promoter compound. The preferred variant of step (a') is the simultaneous deposition of silver and promoter compound. The concentrations of silver compound and promoter compound best used in the solutions for a particular support material can be easily and quickly determined by preliminary experiments and analytical determination of the levels of actually deposited compounds.

The impregnating can be carried out by one of the customary procedures, namely advantageously by soaking (dipping or dousing) the support material in a vessel in the impregnating solution, which penetrates into the pores of the support material by absorption and/or by capillary action, and the silver compound and promoter compound deposit onto the support material. Excess impregnating solution is then separated off (for example by pouring it off, allowing it to drip off, by filtering off the support material or by centrifuging), and the fully saturated support material is then dried. The amount of impregnating solution is generally chosen to be such that the volume of impregnating solution present is larger than the volume of support material to be impregnated. In general, the volume of impregnating liquid taken is 0.5 to 3 times, preferably equal to or twice, the volume of support material. The impregnating time, i.e. the time during which the support material is in contact with the impregnating liquid, should clearly be chosen in such a way that the required amount of silver compound and promoter compound to be deposited is applied to the support. The time generally amounts to 5 to 60 minutes and depends, in particular, on the concentration of silver compound and promoter compound in the impregnating solution, on the support material used and on its particular absorbence. The impregnating temperature used can vary within wide limits. Impregnating is generally carried out at room temperature. It is also possible to use elevated temperatures to speed up the impregnating step. The impregnating temperature accordingly is, as a rule, 15 to 80° C., preferably 20° to 50° C. Impregnating is generally carried out under atmospheric pressure.

The product of an impregnating step (an impregnated support material) is generally dried at a temperature of 20° to 150° C., preferably 50° to 120° C. The solvent can be evaporated off by means of, for example, rack dryers, rotary tube dryers or the passage of hot inert gases, such as nitrogen and/or carbon dioxide. The temperature clearly depends on the boiling point of the solvent of the impregnating liquid.

The silver compound deposited onto the support material is reduced to metallic silver by heating. The thermal reduction of silver compounds generally requires a temperature of 170° to 400° C., preferably 200° to 350° C. The heating to these temperatures can be carried out in, for example, a rack dryer, a rotary tube dryer or an electrically heated tube or by passing over a suitably hot inert gas, such as air, nitrogen, carbon dioxide or a mixture thereof. The silver compound can also be converted into metallic silver by means of super heated steam. The heating time required at the temperatures mentioned is generally 0.2 to 5 hours, and it should preferably be 0.3 to 1 hour. As the silver compound decomposes, a firmly adhering deposit of metallic silver particles forms on the support material (the promoter compounds are not reduced to the corresponding metal; the alkali metals potassium, rubidium and cesium are thus essentially present in the form of their cations and not as free alkali metals). The silver (the silver particles) is generally apparent in the form of firmly adhering discrete particles which are essentially uniformly distributed, which do not hang together and which have a diameter of less than 1.5 μm. The silver particles generally have diameters from 0.1 to 1 μm and a mean diameter of 0.2 to 0.7 μm.

The following part of the text specifies suitable silver compounds, silver-complexing agents, promoter compounds and suitable solvents and advantageous impregnating solutions.

The silver compounds used are preferably silver salts. Examples of suitable inorganic salts are silver nitrate and silver carbonate. Examples of suitable organic salts are salts of monobasic or polybasic carboxylic acids and hydroxy carboxylic acids having up to 6 carbon atoms, such as silver acetate, silver lactate or silver oxalate. The silver compounds are water-soluble and decompose to metallic silver when heated.

It is advantageous to use a silver-complexing agent to increase the solubility of the silver compound. Known complexing agents of this type are ammonia, aminoacids and/or amines, such as alkylenediamines having 2 to 4 carbons atoms, for example ethylenediamine, alkanolamines having 2 to 4 carbons atoms, for example ethanolamine, mono- di- and trialkylamines having 1 to 4 carbon atoms (in the alkyl group), for example methylamine, isopropylamine, isobutylamine or secondary butylamine, or polyamines. The preferred complexing agents mentioned are the alkylamines, preferably the monoalkylamines having 1 to 4 carbon atoms. The complexing agents are added in an amount which is sufficient to give quantitative conversion of the silver compound into the silver-amino complex. This generally requires a small molar excess of amino groups. Since a silver cation binds two amino groups, at least two amino groups have to be used per mole of silver cation.

Suitable promoter compounds are the salts, hydroxides and oxides of said metals potassium, rubidium and cesium, the salts being preferred, but it is not critical what the anion is. Specific examples of inorganic salts are the nitrate, chlorate, carbonate and phosphate. Examples of organic salts are those of monobasic or polybasic carboxylic acids and hydroxycarboxylic acids having up to 6 carbon atoms, for example the formate, acetate, oxalate, citrate and lactate. The promoter compounds, like the silver compounds, are water-soluble.

Suitable solvents for the silver and promoter compounds are water, aliphatic alcohols having 1 to 5, preferably 1 to 3, carbon atoms, such as methanol, ethanol, propanol or isopropanol, aliphatic ketones having 3 to 5 carbon atoms, such as acetone, aliphatic and cyclic ethers, such as diethyl ether, methyl ethyl ether, dipropyl ether and dioxane, esters, such as methyl acetate and ethyl acetate, carboximides, such as dimethylformamide, and nitriles, such as acetonitrile, and mixtures thereof. If silver compounds and silver and promoter compounds are present, water is the preferred solvent, and if promoter compounds alone are present, aliphatic alcohols having 1 to 3 carbon atoms (and, if appropriate, containing a small amount of water as a solubilizer) are preferred for use as solvent.

For step (a) of the novel way of preparing a catalyst, an advantageous impregnating solution essentially consists of (1) a (water-soluble and heat-decomposable) silver salt in an amount of 30 to 40% by weight, (2) at least one (water-soluble) promoter salt, preferably a cesium salt, in an amount of 0.02 to 0.04% by weight, (3) water in an amount of 20 to 30% by weight, and (4) a monoalkylamine having 1 to 4 carbon atoms as a complexing agent for the silver salt in an amount of 30 to 40% by weight, weight percentages being relative to the weight of the solution. An advantageous impregnating solution for step (c) essentially consists of (1) a (water-soluble and heat-decomposable) silver salt in an amount of 30 to 40% by weight, (2) at least one (water-soluble) promoter salt, preferably a cesium salt, in an amount of 0.045 to 0.07% by weight, (3) water in an amount of 20 to 30% by weight, and (4) a monoalkylamine having 1 to 4 carbon atoms as a complexing agent for the silver salt in an amount of 30 to 40% by weight, weight percentages being relative to the weight of the solution. (It will be readily understood that the concrete concentration of silver salt and promoter salt in the two impregnating solutions depends on the amount of silver and promoter which is intended to be applied to the support.) It is not necessary to subject the product contained in step (c) to a special drying before it is treated in step (d). The solvent is evaporated off anyhow in step (d) in the course of heating up to the reduction temperature.

The following impregnating solutions are preferably used for step (a') of the novel way of preparing a catalyst: the solution for applying the silver to the support material by variant 1 essentially consists of (1) a (water-soluble and heat-decomposable) silver salt in an amount of 30 to 40% by weight, (2) water in an amount of 20 to 30% by weight, and (3) a monoalkylamine having 1 to 4 carbon atoms as a complexing agent for the silver salt in an amount of 30 to 40% by weight; the solution for applying the promoter by variant 1 essentially consists of (1) at least one (water-soluble and/or alcohol-soluble) promoter salt, preferably a cesium salt, in an amount of 0.01 to 0.03% by weight, (2) water in an amount of 0 to 5% by weight, and (3) an aliphatic alcohol having 1 to 3 carbon atoms as the remainder, i.e. the percentage difference to 100% by weight; and the solution for the simultaneous application of silver compound and promoter compound by variant 2 of step (a') essentially consists of (1) a (water-soluble and heat-decomposable) silver salt in an amount of 30 to 40% by weight, (2) at least one (water-soluble) promoter salt, preferably a cesium salt, in an amount of 0.01 to 0.03% by weight, (3) water in an amount of 20 to 30% by weight, and (4) a monoalkylamine having 1 to 4 carbon atoms as a complexing agent for the silver salt in an amount of 30 to 40% by weight; weight percentages being relative to the weight of the solution. An advantageous impregnating solution for step (c') essentially consists of (1) at least one (water-soluble and/or alcohol-soluble) promoter salt, preferably a cesium salt, in an amount of 0.04 to 0.08% by weight, (2) water in an amount of 0 to 5% by weight, and (3) an aliphatic alcohol having 1 to 3 carbon atoms as the remainder, i.e. the percentage difference to 100% by weight, weight percentages being relative to the weight of the solution. (It will be readily understood that the concrete concentration of silver salt and promoter salt in the two impregnating solutions depends on the amount of silver and promoter which is intended to be applied to the support).

Variant 1 of step (a') is preferably carried out with an intermediate drying, i.e. the impregnated material is dried after having been impregnated with the solution of the silver compound and before being impregnated with the promoter compound. It is not necessary to subject the product obtained in step (a') to a special drying before it is treated in step (b'), for the solvent can also be evaporated from the support material in step (b'), where heating to elevated temperatures takes place anyhow.

In the second method of the process of the invention, it was found advantageous, in some cases, to subject the silver catalyst obtained by step (a') to (d') to a wash in which the catalyst is brought into contact with a solvent in which the promoter compound applied to the support is soluble. The wash is carried out in particular when the finished catalyst contains too much promoter compound, for the excess can be removed in a simple manner by washing. The wash can also be carried out to establish a certain optimum alkali metal concentration in the finished catalyst in a rapid and simple manner.

The liquid used for the wash is preferably water, an aliphatic alcohol having 1 to 4 carbon atoms or mixtures thereof. A particularly preferred washing liquid consists of methanol, ethanol, propanol and/or isopropanol and water in an amount of 0 to 20% by weight, relative to the weight of the washing liquid.

The wash itself can be carried out by procedures known per se, in which the catalyst is brought into contact with the washing liquid and then separated therefrom and dried. In a preferred procedure, the wash is carried out by dousing the catalyst in a vessel with the washing liquid and is then separated therefrom by centrifuging, gravity filtering, filtering with suction or simply decanting. The length of time for which the catalyst is left in contact with the washing liquid is in principle not critical. It depends in particular on the amount of promoter compound to be dissolved off, and is generally 0.2 to 20 minutes, preferably 0.5 to 5 minutes. It is generally sufficient to perform one washing process. It can, nevertheless, be of advantage to carry out a batchwise wash by washing the catalyst 2 to 5 times, preferably 2 or 3 times, each time preferably with fresh (new, unused) washing liquid. The amount of washing liquid (for a single or repeated wash) depends on the amount of catalyst to be washed, and should of course be sized so as to bring into contact with the liquid all of the catalyst, if need be by stirring. The amount (in parts by volume) is advantageously at least about ⅓ of the amount of catalyst (in parts by volume), but it is preferable to use about an equal to 3 times the amount of washing liquid. The temperature and pressure during the wash is not critical; the wash can be carried out under atmospheric or superatmospheric pressure. The wash is generally carried out at a temperature of 15° to 80° C., preferably 20° to 50° C.

The washed catalyst can be dried, for example, by means of an inert gas, such as nitrogen, carbon dioxide, air or mixtures thereof, and/or by heating the catalyst, and to speed up the drying it is also possible to use reduced pressure. The temperature at which the drying is carried out is not critical. It preferably allows for the boiling point of the washing liquid used. Preferred drying temperatures range from 20° to 150° C., preferably from 50° to 120° C.

In the silver catalyst of the invention, the silver is essentially uniformly distributed over the inner and outer surfaces of the support material. The alkali metal (the alkali metal compound), on the other hand, is unevenly (asymmetrically) distributed. The outer layers of the substrate contain a higher promoter concentration than the inner layers. On a substrate there is thus a promoter concentration gradient of the form that the promoter concentration is higher on the outside than on the inside.

The silver catalyst of the invention has a high activity and selectivity and a long operating life. Its long operating life means that it retains its high effectiveness for a relatively long period of use. This is associated with the further advantage that the silver catalyst of the invention need be replaced or regenerated only at relatively infrequent intervals.

The novel process for preparing silver catalysts is simple and easy to carry out. It is free of any complicated or involved steps, nor does it require special impregnating solutions.

The conditions to be employed when using the novel silver catalyst in the manner of the invention, such as temperature, pressure, residence time, diluents, moderating substances to control the catalytic oxidation of ethylene with oxygen, recycling, operation measures to increase the ethylene oxide yield, and the like, are known in principle. The reaction temperature is generally 150° to 400° C., preferably 200° to 300° C., and the reaction pressure is 0.15 to 3 Mpa, preferably 1 to 2 Mpa. The feed mixture used generally contains 5 to 30 mole % of ethylene, 3 to 15 mole % of oxygen and, as remainder, inert gases, such as nitrogen, carbon dioxide, steam, methane, ethane, argon and the like, as well as vinyl chloride, 1,2-dichloroethane and the like as moderating substances. The ethylene oxide is isolated in a customary manner from the reaction product, and the gas mixture is conventionally purified, if desired, and returned.

In a preferred embodiment of the use of the silver catalysts of the invention, ethylene oxide is prepared by oxidizing ethylene at a temperature of 200° to 270° C. in the presence of the novel silver catalyst with a gas mixture containing about 8.5% by weight of oxygen.

The invention will now illustrated in more detail by means of examples.

Examples 1 to 4 relate to the first method, and Examples 5 to 8 to the second method, of the novel process of preparing a catalyst.

EXAMPLE 1

To prepare a catalyst of the invention, a solution was prepared from
13.03 g (37.9441% by weight) of silver nitrate
9.10 g (26.4997% by weight) of distilled water
0.01 g ( 0.0291% by weight) of cesium nitrate
12.20 g (35.5271% by weight) of isobutylamine.

The SA 5552 support material from the Norton Company, namely α-alumina in the form of cylinders having a specific surface area of 0.3 m²/g, was completely dipped at room temperature for 15 minutes into this solution. When excess impregnating solution had dripped off through a sieve, the moist support material was dried at 105° C. for 30 minutes in an air/nitrogen atmosphere (steps a and b).

When the half-finished catalyst had cooled down, it was impregnated once more in the manner described above with a solution consisting of
13.03 g (36.6557% by weight) of silver nitrate
10.00 g (28.1318% by weight) of distilled water
0.017 g ( 0.0478% by weight) of cesium nitrate
12.50 g (35.1647% by weight) of isobutylamine and dried (step c).

The drying was followed by a reduction for half an hour in a preheated rotary tube furnace at 300° C. through which an air/nitrogen mixture flowed (step d). This gave a silver catalyst containing 11.4% by weight of silver and 0.015% by weight of cesium.

74% by weight of the total amount of silver and 33% by weight of the total amount of cesium had been applied in the first impregnating step, followed by the respective remainders in the second impregnating step.

20 ml of the catalyst thus prepared were introduced into a stainless steel pressure reactor and were charged, at 210° C. and a gas pressure of 1.3 Mpa, with an operating gas consisting of 30% by volume of ethylene, 50% by volume of methane, 8.5% by volume of oxygen, 0.0003% by volume of vinyl chloride and a nitrogen remainder. The weight hourly space velocity was 3000 liters (S.T.P.) of gas per liter of catalyst per hour.

The gas leaving the reactor contained 1.5% by volume of ethylene oxide from which the selectivity (=moles of ethylene oxide formed per mole of converted ethylene) was calculated as 82.1% at an ethylene conversion of 6%.

In the course of a long-term trial under the above-mentioned conditions, the selectivity was found to decrease by only 0.3 point (i.e. down to 81.8%) in 4 months.

EXAMPLE 2

(Comparative Example)

In this comparative Example, the entire amount of cesium and the entire amount of silver were applied in only one impregnating step.

The support material of Example 1 was soaked only once with a solution consisting of
31.5 g (49.4910% by weight) of silver nitrate
15.6 g (24.5098% by weight) of distilled water
0.048 g ( 0.0754% by weight) of cesium nitrate
16.5 g (25.9238% by weight) of ethylenediamine
and was dried and reduced, both steps being carried out as in Example 1. The finished catalyst contained 11.3% by weight of silver and 0.016% by weight of cesium.

The following observations were made in the course of a 4 month test on this catalyst under the conditions of Example 1:
Temperature required for 1.5% by volume of ethylene oxide: 218° C.
selectivity at a 6% $C_2H_4$ conversion: 79.3%
selectivity after 1 month: 79.1%

EXAMPLE 3

In this example of the invention, a solution was prepared from
12.000 g (37.4859% by weight) of silver nitrate
9.000 g (28.1145% by weight) of distilled water
0.012 g ( 0.0375% by weight) of cesium acetate
11.000 g (34.3621% by weight) of secondary butylamine.

The SAHM support material supplied by United Catalyst, namely α-alumina in the form of spheres having a diameter of 8 mm and a specific surface area of 0.2 m²/g, was dipped for 10 minutes into this solution in the manner described in Example 1, and dried.

When the half-finished catalyst had cooled down, it was impregnated once more with a solution consisting of
12.000 g (37.4789% by weight) of silver nitrate
9.000 g (28.1092% by weight) of distilled water
0.018 g ( 0.0562% by weight) of cesium acetate
11.000 g (34.3557% by weight) of secondary butylamine
and dried. The drying was followed by a reduction for 20 minutes in a preheated glass tube at 280° C., as a furnace (through which 40 liters of air and 20 liters of nitrogen were blown per hour).

This gave a silver catalyst containing 11.5% by weight of silver and 0.019% by weight of cesium.

68% by weight of the total amount of silver and 37% by weight of the total amount of cesium had been applied in the first impregnating step, followed by the respective remainders in the second impregnating step.

20 ml of the finished catalyst were subjected for 4 months in a pressure apparatus to the test described in Example 1, and the following observations were made:
Temperature required for 1.5% by volume of ethylene oxide: 222° C.
selectivity at a 6% $C_2H_4$ conversion: 81.8%
selectivity after 4 months: 81.5%

EXAMPLE 4

In this example, a cesium salt and rubidium salt were used as promoter. Example 3 was followed in other respects.

The solution for the first impregnating step had the following composition:
12.000 g (37.4906% by weight) of silver nitrate
9.000 g (28.1180% by weight) of distilled water
0.005 g ( 0.0156% by weight) of cesium carbonate
0.003 g ( 0.0094% by weight) of rubidium nitrate
11.000 g (34.3664% by weight) of secondary butylamine.

Solution for the second impregnating step:
12.000 g (36.8992% by weight) of silver nitrate
9.500 g (29.2119% by weight) of water
0.012 g ( 0.0369% by weight) of cesium carbonate
0.009 g ( 0.0277% by weight) of rubidium nitrate
11.000 g (33.8243% by weight) of secondary butylamine.

The finished catalyst contained 11.2% by weight of silver, 0.013% by weight of cesium and 0.008% by weight of rubidium. 71% by weight of the total amount of silver and 25% by weight of the total amount of promoter had been applied in the first impregnating step, followed by the remainders in the second impregnating step.

The Example 1 test for 2 months produced the following result:
Temperature required for 1.5% by volume of ethylene oxide: 226° C.
selectivity at a 6% $C_2H_4$ conversion: 81.7%
selectivity after 2 months: 81.5%.

EXAMPLE 5

The support material used for preparing a catalyst of the invention was SA 5552 from the Norton Company, i.e. α-alumina in the form of spheres having a diameter of 8 mm and a specific surface are of 0.3 m²/g. The support material was evacuated in a glass flask, and all of it was then doused with a silver salt and cesium salt solution consisting of
30.000 g (38.4556% by weight ) of silver nitrate
20.000 g (25.6371% by weight) of distilled water
28.000 g (35.8919% by weight) of isobutylamine
0.012 g ( 0.0154% by weight) of cesium nitrate.

The support material in the impregnating solution was left to stand for 15 minutes, and excess solution was then decanted off. The support material was dried at 110° C. in a nitrogen-flushed drying cabinet for 45 minutes (step a').

The dry sample was then heated at 280° C. for 30 minutes in a glass tube through which an air/nitrogen mixture was blown (40 liters of air and 20 liters of nitrogen per hour). This reduced the silver salt to give a catalyst containing 8.6% by weight of silver and 0.0038% by weight of cesium (step b').

When the unfinished catalyst had cooled down to room temperature it was then (step c') soaked with the following cesium salt solution:
methanol 95.000% by weight
cesium nitrate 0.045% by weight
distilled water 4.955% by weight,
by being completely covered with the solution in a vessel and left to stand at room temperature for 10 minutes. Decanting and drying at 110° C. in a nitrogen-flushed drying cabinet (step d') gave a catalyst containing 0.0125% by weight of cesium and 8.6% by weight of silver (the total amount of silver and 30% by weight of the total amount of cesium were thus applied in the first impregnating step, followed by the remainder of cesium in the second impregnating step).

25 ml of the catalyst thus prepared were tested at 200° C. under atmospheric pressure in a reactor by means of a gas mixture consisting of 30% by volume of ethylene, 50% by volume of methane, 8.5% by volume of oxygen, 0.0003% by volume of vinyl chloride and a nitrogen remainder. The weight hourly space velocity was 400 liters (S.T.P.) of gas per liter of catalyst per hour. The gas leaving the reactor contained 1.3% by volume of ethylene oxide, from which the selectivity (i.e. the moles of ethylene oxide formed per mole of converted ethylene) was calculated as 81.5% at an ethylene conversion of 5%.

In the course of a long-term trial under the above-mentioned conditions, the selectivity was found to decrease by only 0.3 point to 81.2% in 3 months.

EXAMPLE 6

In this example of the invention, the support material was the SAHM grade supplied by United Catalyst, i.e. an α-alumina in the form of spheres having a diameter of 8 mm and a specific surface area of 0.2 $m^2/g$. All of it was covered in a beaker with a solution of
30.000 g (39.4659% by weight) of silver nitrate
20.000 g (26.3106% by weight) of distilled water
22.000 g (28.9417% by weight) of secondary butylamine
4.000 g (5.2621% by weight) of ethylenediamine
0.015 g (0.0197% by weight) of cesium nitrate,
and was left to stand for 15 minutes. Excess impregnating solution was decanted off, and the support material was dried at 100° C. for 30 minutes in a drying cabinet with a nitrogen atmosphere (step a').

The silver nitrate on the support was reduced to metallic silver in a drying cabinet (flushed per hour with 80 liters of air and 60 liters of nitrogen) by heating at 250° C. for 1 hour (step b').

The unfinished catalyst obtained contained 8.6% by weight of silver and 0.0045% by weight of cesium.

The unfinished catalyst was soaked for 15 minutes in the following cesium salt solution (step c'):
methanol: 95.00% by weight
distilled water: 4.95% by weight
cesium acetate: 0.05% by weight.

Decanting and drying at 100° C. for 30 minutes (step d') gave a silver catalyst which contained 8.6% by weight of silver and 0.0107% by weight of cesium, of which total amount of cesium 40% by weight had been applied in the first impregnating step.

This catalyst was tested in the manner of Example 1 in a long-term trial of 3 months, which had the following result:
Temperature required for 1.3% by volume of ethylene oxide: 196° C.
selectivity at a 5% $C_2H_4$ conversion: 81.6%
selectivity after 3 months: 81.3%.

EXAMPLE 7

(Comparative Example)

In this comparative Example, the total amount of silver and the total amount of cesium were applied in one impregnating step (one-step simultaneous application of the total amount of silver and promoter). The support and the procedure were as in Example 1.

The impregnating solution had the following composition:
30.00 g (38.4369% by weight) of silver nitrate
20.00 g (25.6246% by weight) of distilled water
28.00 g (35.8744% by weight) of secondary butylamine
0.05 g (0.0641% by weight) of cesium nitrate.
The finished catalyst contained 8.5% by weight of silver and 0.0130% by weight of cesium.

The catalyst was tested for 2 months under the conditions described in Example 1, with the following result:
Temperature required for 1.3% by volume of ethylene oxide: 193° C.
selectivity at a 5% $C_2H_4$ conversion: 80.2%
selectivity after 2 months: 80.1%.

EXAMPLE 8

(Comparative Example)

In this comparative Example, the total amount of cesium was applied in the second impregnating step, after the total amount of silver had been applied in the first impregnating step. The support and the procedure were as in Example 1.

The impregnating solution for the first impregnating step had the following composition:
30.0 g (38.46% by weight) of silver nitrate
20.0 g (25.64% by weight) of distilled water
28.0 g (35.90% by weight) of secondary butylamine
The catalyst obtained on reduction of the applied silver nitrate had a silver content of 8.6% by weight. The total amount of cesium was then applied by means of the following solution:
methanol: 95.00% by weight
distilled water: 4.93% by weight
cesium nitrate: 0.07% by weight.
The finished catalyst contained 8.6% by weight of silver and 0.0135% by weight of cesium.

This catalyst was tested for 1 month under the conditions described in Example 1, with the following result:
Temperature required for 1.3% by volume of ethylene oxide: 194° C.
selectivity at a 5% $C_2H_4$ conversion: 79.8%
selectivity after 1 month: 79.6%.

We claim:
1. A method for making a silver catalyst consisting essentially of 3 to 20 percent of silver and 0.003 to 0.05 percent of a promoter which is at least one of potassium, rubidium, and cesium, said percentages being by weight of said catalyst, present on a heat resistant porous support consisting of aluminum oxide having a specific surface area from 0.1 to 1 $m^2/g$ (as measured by the method of Brunauer, Emmett and Teller), which method comprises:

(a) in a first impregnating step, simultaneously applying to said support from 55 to 85 percent by weight of the total amount of said silver and from 15 to 45 percent by weight of the total amount of said promoter in the form of an impregnating solution containing compounds of silver and of said promoter;
(b) drying the impregnated support obtained in step (a);
(c) in a second impregnating step, simultaneously applying to the dried support the remaining amount of said silver and of said promoter in the form of an impregnating solution containing compounds of silver and of said promoter; and
(d) heating the impregnated support obtained in step (c) to reduce the applied silver compound to metallic silver.

2. A method as in claim 1 wherein, in step (a) from 60 to 75 percent by weight of the total amount of silver and from 25 to 40 percent by weight of the total amount of promoter are applied.

3. A silver catalyst made by the method of claim 1.

4. A silver catalyst as in claim 3 containing from 7 to 14 percent of silver by weight of said catalyst.

5. A silver catalyst as in claim 3 containing from 0.008 to 0.035 percent of promoter by weight of said catalyst.

6. A silver catalyst as in claim 3 wherein said promoter is cesium.

7. A method for making a silver catalyst consisting essentially of 3 to 20 percent of silver and 0.003 to 0.05 percent of a promoter which is at least one of potassium, rubidium, and cesium, said percentages being by weight of said catalyst, present on a heat resistant porous support consisting of aluminum oxide having a specific surface area from 0.1 to 1 $m^2/g$ (as measured by the method of Brunauer, Emmett and Teller), which method comprises:

(a) (i) simultaneously applying to said support the total amount of silver and from 15 to 45 percent by weight of the total amount of said promoter in the form of an impregnating solution containing compounds of silver and of said promoter in a single impregnating step, or
(a) (ii) successively applying to said support the total amount of silver in the form of an impregnating solution containing a compound of silver in a first impregnating step and from 15 to 45 percent by weight of the total amount of said promoter in the form of an impregnating solution containing a compound of said promoter in a second impregnating step;
(b) heating the impregnated support obtained in step (a) (i) to reduce the applied silver compound to metallic silver;
(c) applying to the supported catalyst obtained in step (b) the remaining amount of said promoter in the form of an impregnating solution containing a compound of said promoter in a further impregnation step; and
(d) drying the impregnated supported catalyst obtained in step (c).

8. A method as in claim 7 wherein, in step (a), from 20 to 35 percent by weight of the total amount of promoter is applied.

9. A silver catalyst made by the method of claim 7.

10. A silver catalyst as in claim 7 containing from 7 to 14 percent of silver by weight of said catalyst.

11. A silver catalyst as in claim 7 containing from 0.008 to 0.035 percent of promoter by weight of said catalyst.

12. A silver catalyst as in claim 7 wherein said promoter is cesium.

* * * * *